(12) United States Patent
Beasley, Jr.

(10) Patent No.: US 6,506,746 B2
(45) Date of Patent: *Jan. 14, 2003

(54) METHOD FOR TREATING COGNITIVE DYSFUNCTION

(75) Inventor: Charles M Beasley, Jr., Indianapolis, IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,918

(22) PCT Filed: May 30, 1995

(86) PCT No.: PCT/US95/06859

§ 371 (c)(1),
(2), (4) Date: Nov. 25, 1997

(87) PCT Pub. No.: WO96/38151

PCT Pub. Date: Dec. 5, 1996

(65) Prior Publication Data

US 2002/0177590 A1 Nov. 28, 2002

(51) Int. Cl.[7] .............................................. A61K 31/55
(52) U.S. Cl. ...................... 514/220; 514/878; 514/879
(58) Field of Search ................................ 514/220, 878, 514/879

(56) References Cited

U.S. PATENT DOCUMENTS

| 5,229,382 A | 7/1993 | Chakrabarti et al. ........ 514/220 |
| 5,371,079 A | 12/1994 | Kukla et al. ................. 514/220 |

FOREIGN PATENT DOCUMENTS

EP    0 454 436    10/1991

OTHER PUBLICATIONS

Meltzer, Herbert Y. (1) et al: Recent advances in the pharmacotherapy of schizophrenia.: Acta Psychiatrica Scandinavia. (1994) vol. 99, Mo. Suppl. 384. pp 95–101.

Moore N A et al: "The behavorial pharmacology of olanzapine, a novel "atypical" antipsychotic agent." Journal of Pharmacology and Experimental Therapeutics, (Aug. 1992) 262 (2) 545–551.

Accession No: 95:399727 PROMT. "Zyprex: Lilly's Next wonder Drug?" Indianapolis Star (IN), (Sep. 17, 1995), pp. E1.

Chemical Abstracts, vol. 116, No. 9, issued Mar. 2, 1992, Chakrabarti, et al., p. 283, column 1, abstract No. 83703u, Eur. Pat. Appl. 0,454,436.

*Primary Examiner*—Frederick Krass
(74) *Attorney, Agent, or Firm*—Nelsen L. Lentz; Arleen Palmberg

(57) ABSTRACT

The invention provides a method of treating a cognitive dysfunction comprising administering an effective amount of 2-methyl-4-(4-methyl-1-piperazinyl)-10H-thieno(2,3-b) [1,5]benzodiazepine.

4 Claims, No Drawings

METHOD FOR TREATING COGNITIVE DYSFUNCTION

This application is a 371 of PCT/US95/06859, filed May 30, 1995.

This invention provides a method of using 2-methyl-4-(4-methyl-1-piperazinyl)-10H-thieno[2,3-b][1,5]benzodiazepine, for the treatment of cognitive dysfunction.

Alzheimer's Disease is a degenerative brain disorder characterized clinically by progressive loss of memory, cognition, reasoning, and judgment. Eventually, a global defect develops that involves all aspects of higher cortical function. Initiative diminishes, and the patient may become distractible. In addition to the decreased cognitive function, specific disturbances of speech, motor activity, and recognition of perceptions may be discernible. Normal personality traits may become exaggerated or caricatured. The initial affective change may be dominated by irritability, with periods of anger and violence. The patient commonly exhibits impoverished thought process and delusions. As the disease progresses uncontrollable agitation commonly develops. To date, Alzheimer's Disease has proven to be incurable.

Palliative treatments to alleviate the symptoms of cognitive dysfunctions of disease processes such as Alzheimer's Disease could improve the quality of life for both the patient and the patient's caregiver. Such treatments could minimize or delay the emergence of symptoms requiring hospitalization or institutional care. Therefore, such treatments are desirable for both health economic purposes and for the enhancement of the quality of life when a cognitive dysfunction is present.

Further, although the cholinergic neurons degenerate, it is characteristic of Alzheimer's Disease that the postsynaptic muscarinic receptors in the forebrain and hippocampus still exist. Muscarinic cholinergic agonists are therefore useful in the treatment of Alzheimer's Disease and in improving the cognitive functions of those afflicted with Alzheimer's Disease.

Surprisingly, and in accordance with this invention, Applicants have discovered that the compound 2-methyl-4-(4-methyl-1-piperazinyl)-10H-thieno[2,3-b][1,5]benzodiazepine can be useful for the treatment of a cognitive dysfunction, particularly Alzheimer's Disease. The compound 2-methyl-4-(4-methyl-1-piperazinyl)-10H-thieno[2,3-b][1,5]benzodiazepine is known and described in U.S. Pat. No. 5,229,382, herein incorporated by reference in its entirety.

The presently claimed invention provides a method for treating a cognitive dysfunction comprising administering an effective amount of 2-methyl-4-(4-methyl-1-piperazinyl)-10H-thieno[2,3-b][1,5]benzodiazepine to a patient in need of such treatment.

Further, the invention provides a method for the palliative treatment of a cognitive dysfunction comprising administering an effective amount of 2-methyl-4-(4-methyl-1-piperazinyl)-10H-thieno[2,3-b][1,5]benzodiazepine to a patient in need of such treatment. The 2-methyl-4-(4-methyl-1-piperazinyl)-10H-thieno[2,3-b][1,5]benzodiazepine compound is particularly useful for the palliative treatment of Alzheimer's Disease.

The 2-methyl-4-(4-methyl-1-piperazinyl)-10H-thieno[2,3-b][1,5]benzodiazepine compound is of the formula

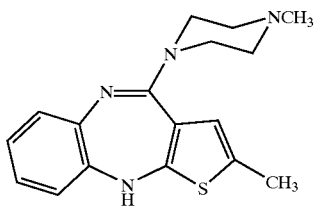

(I)

or an acid addition salt thereof. The free base of formula (I) is 2-methyl-4-(4-methyl-1-piperazinyl)-10H-thieno[2,3-b][1,5]benzodiazepine.

The substantially pure crystalline anhydrous Form I 2-methyl-4-(4-methyl-1-piperazinyl)-10H-thieno[2,3-b][1,5]benzodiazepine (Form I) has a typical X-ray powder diffraction pattern substantially as follows, using a Sieman's D5000 diffractometer equipped with a copper radiation source, wherein represents the interplaner spacing:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Form II 2-methyl-4-(4-methyl-1-piperazinyl)-10H-thieno[2,3-b][1,5]benzodiazepine (Form II) has a typical X-ray powder diffraction pattern substantially as follows, using a Sieman's D5000 diffractometer equipped with a copper radiation source, wherein d represents the interplaner spacing:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |

-continued

| d | I/I$_1$ |
|---|---|
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper K of wavelength=1.541A. The interplanar spacings in the column marked "d" are in Angstroms. The typical relative intensities are in the column marked "I/I$_1$". The detector was a Kevex silicon lithium solid state detector.

As used herein "substantially pure" shall refer to anhydrous Form I associated with <5% Form II; and most preferably it shall refer to <2% Form II. It is further preferred that "substantially pure" shall refer to <0.5% non-Form I polymorph.

As used herein "substantially pure" shall refer to anhydrous Form I associated with about <5% Form II; and most preferably it shall refer to about <2% Form II. It is further preferred that "substantially pure" shall refer to <0.5% related substances. When the Form I polymorph is formulated as a pharmaceutical composition, "substantially pure" shall preferably refer to about <15% Form II polymorph; more preferably, the term shall refer to about <10% Form II polymorph when the Form I polymorph is formulated as a pharmaceutical, and it is especially preferred that the term shall refer to about <5% Form II polymorph when the substantially pure substance is formulated.

As used herein, the term "2-methyl-4-(4-methyl-1-piperazinyl)-10H-thieno[2,3-b][1,5]benzodiazepine" refers to a technical grade of 2-methyl-4-(4-methyl-1-piperazinyl)-10H-thieno[2,3-b][1,5]benzodiazepine when no specific solvate or polymorph is named. Typically, the technical grade 2-methyl-4-(4-methyl-1-piperazinyl)-10H-thieno[2,3-b][1,5]benzodiazepine contains less than about 5% undesired related substances and may be a mixed polymorph. Such technical grade 2-methyl-4-(4-methyl-1-piperazinyl)-10H-thieno[2,3-b][1,5]benzodiazepine usually contains less than about 1% undesired related substances.

The term "crude" refers to a form of 2-methyl-4-(4-methyl-1-piperazinyl)-10H-thieno[2,3-b][1,5]benzodiazepine typically associated with undesired polymorph and/or greater than about 5% undesired related substances. Such crude grade 2-methyl-4-(4-methyl-1-piperazinyl)-10H-thieno[2,3-b][1,5]benzodiazepine may contains less than about 1% undesired related substances.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "palliative treatment" shall refer to a treatment designed for the relief of symptoms of cognitive dysfunction, rather than curing the disease. Such symptoms of cognitive dysfunction may include, but are not limited to progressive loss of memory, cognition, reasoning, judgment, aspects of higher cortical function, diminished initiative, excessive distraction, speech, motor activity, recognition of perceptions, exaggerated or caricatured personality traits, irritability, excessive anger, violence, uncontrollable agitation, and delusions. The method of this invention is particularly useful for the treatment of delusions and disturbance in perceptions from such cognitive dysfunction. Further, the method of this invention is especially desirable for the treatment of excessive personality traits, irritability, excessive anger, violence, and uncontrollable agitation.

The term "cognitive dysfunction" shall refer to a dysfunction in the ability of a subject to perceive, reason, remember, and in the ability to acquire knowledge. Such dysfunction may be associated with Alzheimer's Disease, AIDS, and other central nervous system conditions which cause such dysfunction.

The results of pharmacological studies show that 2-methyl-4-(4-methyl-1-piperazinyl)-10H-thieno[2,3-b][1,5]benzodiazepine has muscarinic cholinergic receptor activity. The compound is active at the dopamine D-1 and D-2 receptors as indicated by an IC50 of less than 1 uM in the 3H-SCH233390 (Billard, et al. Life Sciences 35:1885 (1984)) and the 3H spiperone (Seeman et al Nature 216:717 (1976)) binding assays respectively. Further, the anhydrous Form I compound is active at the 5-HT-2 receptor and 5-HT1C receptor. The complex pharmacological profile of the compound provides a medicament which can be useful for the treatment of a cognitive dysfunction.

In vivo animal and clinical observations support that 2-methyl-4-(4-methyl-1-piperazinyl)-10H-thieno[2,3-b][1,5]benzodiazepine has a complex muscarinic receptor subtype profile. For example, rats exposed to an overdose of the compound surprisingly exhibited significant salivation. Further, clinical subjects experienced pupilary constriction rather than the expected pupilary dialation.

The compound 2-methyl-4-(4-methyl-1-piperazinyl)-10H-thieno[2,3-b][1,5]benzodiazepine can be used for the methods of this invention, both in its free base and acid addition salt forms. The acid addition salts are preferably the pharmaceutically acceptable, non-toxic addition salts with suitable acids, such as those of inorganic acids, for example hydrochloric, hydrobromic, nitric, sulphuric or phosphoric acids, or of organic acids, such as organic carboxylic acids, for example glycollic, maleic, hydroxymaleic, fumaric, malic, tartaric, citric or lactic acid, or organic sulphonic acids for example methane sulphonic, ethane sulfonic, 2-hydroxyethane sulfonic, p-toluene-sulfonic or naphthalene-2-sulfonic acid.

The compound 2-methyl-4-(4-methyl-1-piperazinyl)-10H-thieno[2,3-b][1,5]benzodiazepine can be prepared using a process which comprises (a) reacting N-methylpiperazine with a compound of the formula

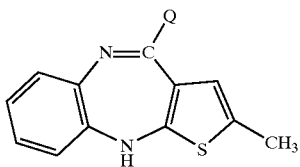

(II)

in which Q is a leaving group capable of being split off, or
(b) ring-closing a compound of the formula

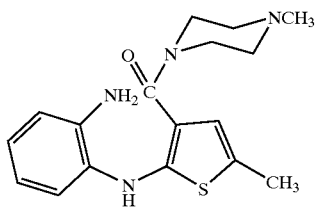

(III)

Appropriate reaction conditions and suitable values of Q can readily be chosen for these processes.

In reaction (a) the radical Q can, for example, be an amino group or a mono- or dialkyl-substituted amino group (each alkyl substituent suitably containing 1 to 4 carbon atoms), hydroxyl, thiol, or an alkoxy, alkylthio or alkylsulphonyl group suitably containing 1 to 4 carbon atoms, for example a methoxy or methylthio group, or a halogen atom, especially a chlorine atom. Preferably, Q is amino (—NH$_2$), hydroxyl or thiol, and amino is most preferred. The reaction is preferably carried out at a temperature of from 50° C. to 200° C.

When Q is amino, the intermediate of formula (II) may also exist in the imino form:

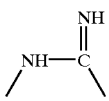

and when Q is hydroxyl or thiol, the intermediates of formula (II) may exist in their amide and thioamide forms:

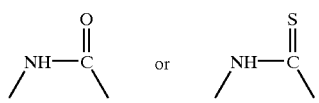

The amidine of formula (II) (Q is —NH$_2$), can be in salt form, for example a salt of a mineral acid such as the hydrochloride, and can be reacted with N-methylpiperazine in an organic solvent such as anisole, toluene, dimethylformamide or dimethyl-sulphoxide, preferably at a temperature range of 100 to 150° C.

The amidine is prepared by condensing a thiophene compound of formula

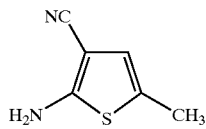

with an ortho-halonitrobenzene, in the presence of a base, for example sodium hydride, in a solvent such as tetrahydrofuran or n-butyl lithium in tetrahydrofuran, or potassium carbonate or lithium hydroxide in dimethylsulphoxide or aqueous sodium hydroxide in dimethylsulfoxide, or with a tetraalkyl-ammonium salt in a two-phase system, to form a nitronitrile of formula:

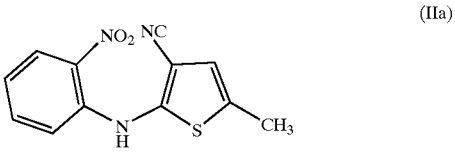

(IIa)

which can be simultaneously reduced and ring-closed to the amidine of formula (II) employing, for example, stannous chloride and hydrogen chloride in aqueous ethanol or, alternatively by reduction with hydrogen and palladium/carbon or ammonium polysulphide followed by acid-catalysed ring closure. The intermediate of formula (IIa) may be isolated using ammonium chloride (NH$_4$Cl) or ammonium acetate (NH$_4$OAc).

When Q is hydroxyl, reaction (a) is preferably carried out in the presence of titanium tetrachloride which has the ability to react with the N-methylpiperazine to form a metal amine complex. Other metal chlorides such as those of zirconium, hafnium or vanadium may also be employed. The reaction can be carried out in the presence of an acid binding agent such as a tertiary amine, for example, triethylamine.

Alternatively, the reaction can be carried out using excess of N-methylpiperazine to act as an acid-binding agent. A suitable organic solvent such as toluene or chlorobenzene can be used as a reaction medium, although the use of anisole is particularly desirable, at least as a co-solvent, in view of its ability to form a soluble complex with TiCl$_4$.

If desired, elevated temperatures, for example up to 200° C., can be used to hasten the reaction and a preferred temperature range for carrying out the reaction is from 80° C. to 120° C.

The intermediate amide of formula (II) (Q is —OH) can be prepared from the corresponding amidine (Q is —NH$_2$) by alkaline hydrolysis, or can be derived from compounds of formula

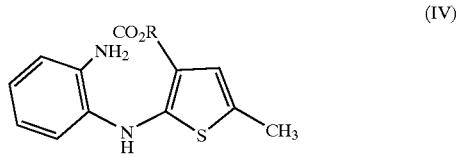

(IV)

in which R is an alleyl group, preferably C$_{1-4}$ alkyl, by ring closure employing, for example, sodium methylsulfinyl methanide in a suitable solvent such as dimethylsulfoxide. Alternatively, the amide can be prepared by ring closure of an amino-acid, employing for example dicyclohexylcarbodiimide (DCC) in a suitable solvent such as tetrahydrofuran. The amino-acid can be obtained for example from the above esters by basic hydrolysis using for example sodium hydroxide in ethanol.

Thioamides of formula (II) (Q is —SH), iminothio-ethers; iminoethers or iminohalides, or other derivatives containing active Q radicals as specified above, tend to be more reactive towards N-methylpiperazine and can usually be reacted without the necessity for the presence of TiCl$_4$, but otherwise employing the same conditions of temperature and solvent.

The thioamide of formula (II) (Q is —SH) can be prepared by treating a solution of the corresponding amide in an anhydrous basic solvent, such as pyridine, with phosphorous pentasulfide. Similarly, the amide can be converted to the iminothioether, iminoether or iminohalide, or other derivatives containing active Q radicals, by treatment with conventional reagents such as for example in the case of the iminochloride, phosphorous pentachloride.

The intermediate compounds of formula (II) in which Q is a leaving group capable of being split off, particularly those in which Q is —NH$_2$, —OH or —SH and when Q is —NH$_2$ salts thereof, are novel compounds, and form a further aspect of the present invention.

With regard to reaction (b) above, the compound of formula (III) may be ring-closed by employing, for example, titanium tetrachloride as catalyst and anisole as solvent, and the reaction is preferably carried out at a temperature of 100° C. to 250° C., for example from 150° C. to 200° C.

The intermediate compound of formula (III) is preferably prepared in situ without isolation by reacting a compound of formula

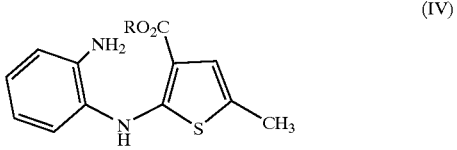

(IV)

in which R is an alleyl group, preferably C$_{1-4}$ alkyl, with N-methylpiperazine, by heating to a temperature of between 30° C. and 120° C., for example about 100° C., in a suitable solvent such as for example anisole, and employing TiCl$_4$ as catalyst.

The compound of formula (IV) can be prepared from the corresponding nitro compound of formula

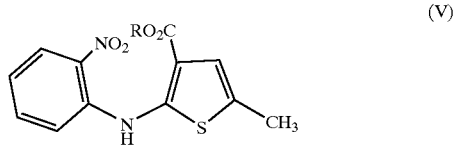

(V)

Such compounds of formula (V) in which R is an allyl group, such as for example C$_{1-4}$ alkyl, are novel and form a further aspect of the invention.

If convenient this nitro compound can be converted to the amine of formula (IV) without isolation, before reaction with N-methylpiperazine. Intermediate compounds of formula (V) can be made by condensation of a thiophene of formula

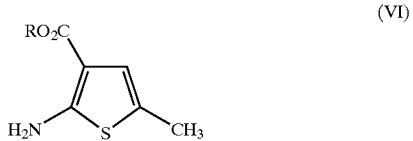

(VI)

with an ortho-halonitrobenzene, preferably ortho fluoro- or chloro-nitrobenzene, in the presence of a base, for example, (a) sodium hydride in a solvent such as for example tetrahydrofuran and at a temperature of from −20° C. to 30° C., or (b) anhydrous potassium carbonate or lithium hydroxide in a solvent such as dimethylsulfoxide at a temperature of from 90° C. to 120° C. The compound of formula (V) is converted to that of formula (IV) by reduction, for example catalytically, employing hydrogen and palladium/carbon, or chemically, employing stannous chloride and hydrogen chloride in aqueous ethanol, or ammonium polysulphide, or zinc in aqueous ammonium chloride.

It will be appreciated that the compound of formula (I) may be isolated per a or may be converted to an acid addition salt using conventional methods.

The compound has an IC$_{50}$ of less than 1 mM in the $^3$H-QNB binding assay described by Yamamura, HI and Snyder, SH in Proc. Nat. Acad. Sci. USA, 71, 1725 (1974) indicating that it has muscarinic-cholinergic activity. Alzheimer's Disease is likely caused by up to 90% degeneration of the muscarinic cholinergic neurons in nucleus basalis, which is part of substantia innominata, and these neurons project to the frontal cortex and hippocampus having a general stimulatory effect on the cognitive functions of the forebrain and hippocampus. Although the cholinergic neurons degenerate, the postsynaptic muscarinic receptors in the forebrain and hippocampus still exist. Therefore, such muscarinic cholinergic agonists can be useful in the treatment of Alzheimer's Disease.

A double-blind multicenter clinical trial was designed to assess the safety and efficacy of 2-methyl-4-(4-methyl-1-piperazinyl)-10H-thieno[2,3-b][1,5]benzodiazepine in 237 elderly patients with cognitive dysfunction, wherein the age of the patients was greater than or equal to sixty-five (65) years of age. Patients were randomized to 2-methyl-4-(4-methyl-1-piperazinyl)-10H-thieno[2,3-b][1,5] benzodiazepine or placebo. Changes in behavioral manifestations were measured using the BEHAVE-AD, BPRS, and CGI rating scales, which are known and available to the skilled artisan. The results of the study suggest that 2-methyl-4-(4-methyl-1-piperazinyl)-10H-thieno[2,3-b][1,5]benzodiazepine can be useful for the treatment of behavioral manifestations of cognitive dysfunction.

The 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of cognitive dysfunction, a dose range of from 1 to 30 mg, preferably 1 to 20 mg per day is suitable. Radiolabelled 2-methyl-4-(4-methyl-1-piperazinyl)-10H-thieno-[2,3-b][1,5]benzodiazepine, can be detected in the saliva and thus the compound can potentially be monitored in patients to assess compliance.

A preferred formulation of the invention is a solid oral formulation comprising from about 1 to about 20 mg or 1 to 10 mg of active anhydrous Form I 2-methyl-4-(4-methyl-1-piperazinyl)-10H-thieno[2,3-b][1,5]benzodiazepine as an effective amount of the active ingredient.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

The 2-methyl-4-(4-methyl-1-piperazinyl)-10H-thieno-[2,3-b][1,5]benzodiazepine compound will normally be administered orally or by injection and, for this purpose, it is usually employed in the form of a pharmaceutical composition.

Accordingly, pharmaceutical compositions comprising 2-methyl-4-(4-methyl-1-piperazinyl)-10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient. For example, one such preferred quick release formulation is described in U.S. Pat. Nos. 5,079,018, 5,039,540, 4,305,502, 4,758,598, and 4,371,516, hereby incorporated by reference. Such formulation most preferably comprises 2-methyl-4-(4-methyl-1-piperazinyl)-10H-thieno[2,3-b][1,5]benzodiazepine, water, hydrolyzed gelatin, and mannitol.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 100 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 75 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor.

The materials for the present invention can be purchased or prepared by a variety of procedures well known to those of ordinary skill in the art. The 2-methyl-4-(4-methyl-1-piperazinyl)-10H-thieno[2,3-b][1,5]benzodiazepine compound can be prepared as described by Chakrabarti in U.S. Pat. No 5,229,382 ('382), herein incorporated by reference in its entirety. It is most desirable to prepare a rapidly dissolving formulation comprising substantially pure crystalline Form I 2-methyl-4-(4-methyl-1-piperazinyl)-10H-thieno[2,3-b][1,5]benzodiazepine. Such substantially pure crystalline Form I 2-methyl-4-(4-methyl-1-piperazinyl)-10H-thieno[2,3-b][1,5]benzodiazepine may be prepared using the techniques described herein by the Preparation section herein infra.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

Compound characterization methods include, for example, x-ray powder pattern analysis, thermogravimetric analysis (TGA), differential scanning calorimetery (DSC), titrametric analysis for water, and $^1$H-NMR analysis for solvent content.

The following examples are provided for purposes of illustration and are not to be construed as limiting the scope of the claimed invention.

Preparation 1

Crystalline Form II 2-methyl-4-(4-methyl-1-piperazinyl)-10H-thieno[2,3-b][1,5]benzodiazepine A 10 gram sample of crude 2-methyl-4-(4-methyl-1-piperazinyl)-10H-thieno[2,3-b][1,5]benzodiazepine was suspended in methylene chloride (100) gm and stirred at ambient temperature (20–25° C.) for a period of 1 hour. The slurry was vacuum filtered and the filtrate was recovered.

The stirred filtrate was chilled to 0–5° C. in an ice bath and the solvent was slowly evaporated under a stream of nitrogen to a thick paste. Approximately ¾ of the solvent was removed by evaporation. A quantity of prechilled methylene chloride (30 gm, 0–5° C.) was mixed into the thick paste. The resulting slurry was vacuum filtered and allowed to air dry on the filter. The isolated solid was further dried in a vacuum oven at 50° C. for a period of 30 minutes. Isolated: 4.8 gm. X-ray powder characterization: Form II+CH$_2$Cl$_2$ Solvate.

The isolated solid was redried in a vacuum oven at 50° C. under a stream of nitrogen for a period of 30 hours. Isolated: 4.5 gm X-ray powder characterization: Form II. (described supra.)

Preparation 2

Form I 2-methyl-4-(4-methyl-1-piperazinyl)-10H-thieno[2,3-b][1,5]benzodiazepine

A sample of ethyl acetate which was saturated with technical grade 2-methyl-4-(4-methyl-1-piperazinyl)-10H-thieno[2,3-b][1,5]benzodiazepine was contacted with Form II 2-methyl-4-(4-methyl-1-piperazinyl)-10H-thieno[2,3-b][1,5]benzodiazepine (0.3 g), a seed of anhydrous Form I 2-methyl-4-(4-methyl-1-piperazinyl)-10H-thieno[2,3-b][1,5]benzodiazepine and stirred at about 25° C. for about 5 hours. The reaction product was isolated by vacuum filtration and dried under ambient conditions. Yield: 0.25 g. X-ray powder analysis indicated that the product was anhydrous Form I 2-methyl-4-(4-methyl-1-piperazinyl)-10H-thieno[2,3-b][1,5]benzodiazepine.

Preparation 3

Technical Grade 2-methyl-4-(4-methyl-1-piperazinyl)-10H-thieno[2,3-b][1,5]benzodiazepine Intermediate 1

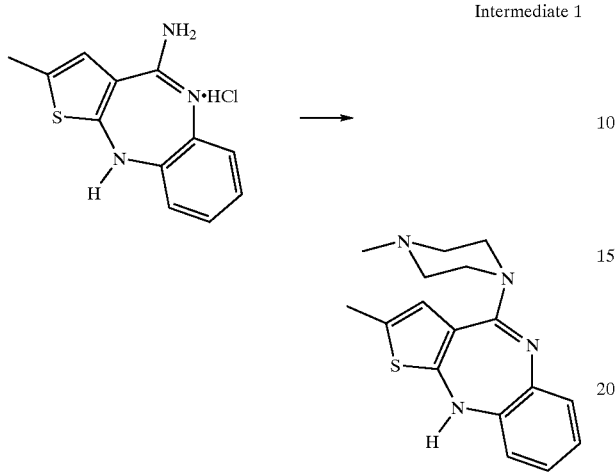

In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b][1,5]benzodiazepine.

Yield: 76.7%; Potency: 98.1%

The procedure of Preparation 3 was repeated substantially as described above and provided a yield of 81% with a potency of 101.1%.

Preparation 4

Technical Grade 2-methyl-4-(4-methyl-1-piperazinyl)-10H-thieno[2,3-b][1,5]benzodiazepine Intermediate 1 (supra) was suspended in DMSO (3.2 vol.) and toluene (4.5 vol.). A portion (≈0.65 vol.) of the solvent was removed by distillation at 120–125° C. The mixture was cooled to 110° C., N-methylpiperazine (NMP, 4.2 equiv.) was added and the mixture heated back to reflux (120–125° C.). Another portion (≈1 vol.) of the solvent was removed by distillation to dry the reaction mixture. A vigorous reflux was desired to drive the reaction to completion (about 7 hrs.) by removing ammonia from the reaction. The product was isolated by the slow addition of water (12.75 vol.) to the cooled (10° C.) reaction solution. The product was collected by filtration and washed with chilled water (2 vol.). The crude 2-methyl-4-(4-methyl-1-piperazinyl)-10H-thieno[2,3-b][1,5]benzodiazepine was dried in vacuo at 60° C. The product was recrystallized from hot toluene (5 vol.) to give a technical grade 2-methyl-4-(4-methyl-1-piperazinyl)-10H-thieno[2,3-b][1,5]benzodiazepine. After drying in vacuo at 50° C., the technical grade 2-methyl-4-(4-methyl-1-piperazinyl)-10H-thieno[2,3-b][1,5]benzodiazepine was recrystallized again from ethyl acetate (10 vol.)/toluene (0.62 vol.)/methanol (3.1 vol.) to give 2-methyl-4-(4-methyl-1-piperazinyl)-10H-thieno[2,3-b][1,5]benzodiazepine as a methanol solvate. The methanol solvate upon drying at >50° C. was converted to an anhydrous technical grade 2-methyl-4-(4-methyl-1-piperazinyl)-10-H-thieno[2,3-b][1,5]benzodiazepine.

Preparation 5

Form I from acetone

A 3.0 g sample of technical grade 2-methyl-4-(4-methyl-1-piperazinyl)-10H-thieno[2,3-b][1,5]benzodiazepine was suspended in acetone (30 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 0.8 g.

Preparation 6

Form I using tetrahydrofuran

An 8.0 g sample of technical grade 2-methyl-4-(4-methyl-1-piperazinyl)-10H-thieno[2,3-b][1,5]benzodiazepine was suspended in tetrahydrofuran (25 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 1.3 g.

Preparation 7

Form I using ethyl acetate

A 270 g sample of technical grade 2-methyl-4-(4-methyl-1-piperazinyl)-10H-thieno[2,3-b][1,5]benzodiazepine was suspended in ethyl acetate (2.7 L). The mixture was heated to about 76° C. and maintained at about 76° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis.

Yield: 197 g.

Preparation 8

Form I from t-butanol

A 1.0 g sample of technical grade 2-methyl-4-(4-methyl-1-piperazinyl)-10H-thieno[2,3-b][1,5]benzodiazepine was suspended in tert-butanol (30 g). The stirred mixture was heated to about 60° C. and maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis.

Yield: 0.3 g.

Preparation 9

Form I from Slurry Conversion of Form II in Toluene

A 0.5 g sample of technical grade 2-methyl-4-(4-methyl-1-piperazinyl)-10H-thieno[2,3-b][1,5]benzodiazepine and a 0.5 g sample of Form II 2-methyl-4-(4-methyl-1-piperazinyl)-10H-thieno[2,3-b][1,5]benzodiazepine were suspended in toluene (5 ml), presaturated with 2-methyl-4-(4-methyl-1-piperazinyl)-10H-thieno[2,3-b][1,5]benzodiazepine. The mixture was stirred in a sealed vial at about ambient temperature for about 22 hours. The resulting product was isolated using vacuum filtration and dried under vacuum at about 45° C. The product was identified as Form I 2-methyl-4-(4-methyl-1-piperazinyl)-10H-thieno[2,3-b][1,5]benzodiazepine using x-ray powder analysis.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno[2,3-b][1,5]benzodiazepine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg 2-methyl-4-(4-methyl-1-piperazinyl)-10H-thieno[2,3-b][1,5]benzodiazepine, respectively, per tablet:

| Names of Ingredients | Quantity (mg/tablet) |
|---|---|
| 1 mg 2-methyl-4-(4-methyl-1-piperazinyl)-10H-thieno[2,3-b][1,5]benzodiazepine per tablet: | |
| Active Ingredient | |
| 2-methyl-4-(4-methyl-1-piperazinyl)-10H-thieno[2,3-b][1,5]benzodiazepine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |
| Magnesium Stearate | 0.42 |
| Subcoating | |
| Hydroxypropyl Methylcellulose | 1.70 |
| Coating | |
| Color Mixture White | 3.47 |
| Polishing | |
| Carnauba Wax | trace |
| Imprinting | |
| Edible Blue Ink | trace |
| 2-methyl-4-(4-methyl-1-piperazinyl)-10H-thieno[2,3-b1[1,5]benzodiazepine 2.5 mg Tablets | |
| Active Ingredient | |
| 2-methyl-4-(4-methyl-1-piperazinyl)-10H-thieno[2,3-b][1,5]benzodiazepine | 2.5 |
| Other Ingredients | |
| Lactose | 102.15 |
| Hydroxypropyl Cellulose | 5.20 |
| Crospovidone | 6.50 |
| Microcrystalline Cellulose | 13.00 |
| Magnesium Stearate | 0.65 |
| Subcoating | |
| Hydroxypropyl Methylcellulose | 2.60 |
| Coating | |
| Color Mixture White | 5.30 |
| Polishing | |
| Carnauba Wax | trace |
| Imprinting | |
| Edible Blue Ink | trace |
| 2-methyl-4-(4-methyl-1-piperazinyl)-10H-thieno[2,3-b][1,5]benzodiazepine 5.0 mg Tablets | |
| Active Ingredient | |
| 2-methyl-4-(4-methyl-1-piperazinyl)-10H-thieno[2,3-b][1,5]benzodiazepine | 5.00 |
| Other Ingredients | |
| Lactose | 156.00 |
| Hydroxypropyl Cellulose | 8.00 |
| Crospovidone | 10.00 |
| Microcrystalline Cellulose | 20.00 |
| Magnesium Stearate | 1.00 |

-continued

| Names of Ingredients | Quantity (mg/tablet) |
|---|---|
| Subcoating | |
| Hydroxypropyl Methylcellulose | 4.00 |
| Coating | |
| Color Mixture White Polishing | 8.16 |
| Carnauba Wax Imprinting | trace |
| Edible Blue Ink | trace |
| 2-methyl-4-(4-methyl-1-piperazinyl)-10H-thieno[2,3-b][1,5]benzodiazepine 7.5 mg Tablets | |
| Active Ingredient | |
| 2-methyl-4-(4-methyl-1-piperazinyl)-10H-thieno[2,3-b][1,5]benzodiazepine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate | 1.50 |
| Subcoating | |
| Hydroxypropyl Methylcellulose | 6.00 |
| Coating | |
| Color Mixture White Polishing | 12.24 |
| Carnauba Wax Imprinting | trace |
| Edible Blue Ink | trace |
| 2-methyl-4-(4-methyl-1-piperazinyl)-10H-thieno[2,3-b][1,5]benzodiazepine 10.0 mg Tablets | |
| Active Ingredient | |
| 2-methyl-4-(4-methyl-1-piperazinyl)-10H-thieno[2,3-b][1,5]benzodiazepine | 10.00 |
| Other Ingredients | |
| Lactose | 312.00 |
| Hydroxypropyl Cellulose | 16.00 |
| Crospovidone | 20.00 |
| Microcrystalline Cellulose | 40.00 |
| Magnesium Stearate | 2.00 |
| Subcoating | |
| Hydroxypropyl Methylcellulose | 8.00 |
| Coating | |
| Color Mixture White Polishing | 16.32 |
| Carnauba Wax Imprinting | trace |
| Edible Blue Ink | trace |

EXAMPLE 4

Pulvule Formulation

A pulvule formulation is prepared by blending the active with silicone starch, and filling it into hard gelatin capsules.

| | per 300 mg capsule |
|---|---|
| Compound of the invention | 30.0 mg |
| Silicone | 2.9 mg |
| Starch flowable | 267.1 mg |

EXAMPLE 5

Tablet Formulation

A tablet formulation is made by granulating the active with appropriate diluent, lubricant, disintegrant and binder and compressing

| | |
|---|---|
| Compound of the invention | 10.0 mg |
| Magnesium stearate | 0.9 mg |
| Microcrystalline cellulose | 75.0 mg |
| Povidone | 15.0 mg |
| Starch, directly compressible | 204.1 mg |

EXAMPLE 6

Aqueous Injection Formulation

An aqueous injection of active is prepared as a freeze-dried plug, for reconstitution in a suitable, sterile diluent before use (to a total volume of 10 ml).

Compound of the invention is contacted with Mannitol N Hydrochloric acid and/or N sodium hydroxide to adjust pH to 5–5.5.

| | |
|---|---|
| Compound of the invention | 20.0 mg |
| Mannitol | 20.0 mg |
| N Hydrochloric acid and/or N sodium hydroxide to adjust pH to 5–5.5. | |

EXAMPLE 7

Controlled Release IM Formulation

A controlled release injection for intramuscular injection is formed from a sterile suspension of micronised active in an oleaginous vehicle.

| | |
|---|---|
| Compound of the invention | 50.0 mg |
| Aluminium stearate | 0.04 mg |
| Sesame oil | 2 ml |

EXAMPLE 8

Capsule Formulation

A formulation is prepared by blending the active with silicone starch and starch, and filling it into hard gelatine capsules.

|  | Per 300 mg capsule |
| --- | --- |
| Compound of the invention | 2.5 mg |
| Starch flowable with 0.96% silicone 220 | 222.5 mg |
| Starch flowable | 75.0 mg |

EXAMPLE 9

2-methyl-4-(4-methyl-1-piperazinyl)-10H-thieno[2,3-b][1,5]benzodiazepine Granules The granules were produced by blending the mannitol and Hydroxymethyl propyl cellulose in a high shear mixer; granulating with the aqueous suspension of 2-methyl-4-(4-methyl-1-piperazinyl)-10H-thieno[2,3-b][1,5]benzodiazepine and polysorbate 20; wet sized and subsequently dried in a fluid bed dryer. These are dry sized and reblended prior to packaging.

| INGREDIENT | MG/SACHET |
| --- | --- |
| 1a. 250 mg Sachets | |
| Active | |
| 2-methyl-4-(4-methyl-1-piperazinyl)-10H-thieno[2,3-b][1,5]benzodiazepine | 250 |
| Other Ingredients | |
| Mannitol | 234.97 |
| Hydroxypropyl methyl cellulose 3 cps | 12.50 |
| Polysorbate 20 | 0.028 |
| 1b. 750 mg Sachets | |
| Active | |
| 2-methyl-4-(4-methyl-1-piperazinyl)-10H-thieno[2,3-b][1,5]benzodiazepine | 750 |
| Other Ingredients | |
| Mannitol | 704.93 |
| Hydroxypropyl methyl cellulose 3 cps | 37.49 |
| Polysorbate 20 | 0.08 |
| 1c. 1000 mg Sachets | |
| Active | |
| 2-methyl-4-(4-methyl-1-piperazinyl)-10H-thieno[2,3-b][1,5]benzodiazepine | 1000 |
| Other Ingredients | |
| Mannitol | 939.90 |
| Hydroxypropyl methyl cellulose 3 cps | 49.99 |
| Polysorbate 20 | 0.11 |

Such granules are most preferably contacted with an acidic medium if a suspension or solution is desired.

I claim:

1. A method for treating a human suffering from a cognitive dysfunction associated with Alzheimer's Disease, comprising administering to said human an effective amount of 2-methyl-4-(4-methyl-1-piperazinyl)-10H-thieno[2,3-b][1,5]benzodiazepine, or a pharmaceutically acceptable salt thereof.

2. A method of claim 1 wherein the 2-methyl-4-(4-methyl-1-piperazinyl)-10H-thieno[2,3-b][1,5]benzodiazepine is substantially pure Form I.

3. A method for treating a human suffering from a cognitive dysfunction associated with HIV Disease, comprising administering to said human an effective amount of 2-methyl-4-(4-methyl-1-piperazinyl)-10H-thieno[2,3-b][1,5]benzodiazepine, or a pharmaceutically acceptable salt thereof.

4. A method for treating a human suffering from a cognitive dysfunction associated with AIDS, comprising administering to said human an effective amount of 2-methyl-4-(4-methyl-1-piperazinyl)-10H-thieno[2,3-b][1,5]benzodiazepine, or a pharmaceutically acceptable salt thereof.

* * * * *